United States Patent [19]

Horvath

[11] Patent Number: 5,046,996
[45] Date of Patent: Sep. 10, 1991

[54] PLANETARY FRICTION DRIVE

[75] Inventor: Eduard Horvath, Vienna, Austria

[73] Assignee: Otto Bock Orthopadische Industrie Besitz-Und Werwaltungs-KG, Duderstadt, Fed. Rep. of Germany

[21] Appl. No.: 381,605

[22] Filed: Jul. 18, 1989

[30] Foreign Application Priority Data

Jul. 18, 1988 [AT] Austria .............................. A 1843/88

[51] Int. Cl.$^5$ ...................... F16H 13/06; F16H 13/10
[52] U.S. Cl. ..................................... 475/197; 623/57; 623/64; 475/183
[58] Field of Search .................. 475/183, 197; 901/19, 901/23; 623/57, 63–65

[56] References Cited

U.S. PATENT DOCUMENTS

| 1,017,910 | 2/1912 | Rennerfelt | 475/197 |
| 3,245,286 | 4/1966 | Hewko | 475/197 X |
| 4,923,477 | 5/1990 | Horvath | 623/57 |

FOREIGN PATENT DOCUMENTS

| 892536 | of 0000 | Fed. Rep. of Germany . | |
| 0237360 | 7/1986 | German Democratic Rep. | 475/183 |
| 0120046 | 10/1978 | Japan | 475/183 |
| 0039763 | 3/1979 | Japan | 475/197 |
| 0001852 | 1/1982 | Japan | 475/197 |
| 0128553 | 8/1983 | Japan | 475/183 |
| 0113357 | 6/1984 | Japan | 475/183 |
| 0136658 | 7/1985 | Japan | 475/197 |
| 0251558 | 11/1987 | Japan | 475/183 |
| 354761 | of 0000 | United Kingdom . | |
| 413802 | of 0000 | United Kingdom | 475/197 |
| 2002066 | of 0000 | United Kingdom . | |
| 0413802 | 7/1934 | United Kingdom | 475/197 |
| 1201480 | 8/1970 | United Kingdom | 475/197 |
| 2135012 | 8/1984 | United Kingdom | 475/183 |

Primary Examiner—Randall L. Green
Assistant Examiner—David H. Willse
Attorney, Agent, or Firm—Herbert Dubno

[57] ABSTRACT

A planetary friction transmission, especially for miniature application as in prosthetic joints and the like, has cylindrical periphery planet wheels pressed by a stationary ring against a conical portion of the drive shaft, the ring being axially shiftable relative to the shaft and on a support. The planet carrier is connected to the planet wheels by pins which extend into the holes of the planet wheels with play.

12 Claims, 1 Drawing Sheet

PLANETARY FRICTION DRIVE

FIELD OF THE INVENTION

My present invention relates to a planetary friction drive for prosthetic devices. The invention is applicable, for example, to the drive of prosthetic joints and, for example, to an artificial hand, e.g. of the type described in the concurrently copending application Ser. No. 07/381,609 filed 18 Jul. 1989, now U.S. Pat. No. 4,923,477 and based upon Austrian application A 1841/88 of 18 Jul. 1988.

BACKGROUND OF THE INVENTION

It is known to provide a planetary friction drive in which the planet wheels roll upon a conical portion of a drive shift and roll in contact with a stationary ring surface. The planet wheels are formed with conical peripheries or peripheral surfaces and have axes which are fixedly positioned with respect to a planet carrier. The planet carrier or entrainment plate is generally resiliently formed in the regions in which the planet wheels are mounted.

It is important with such constructions that the generatrices of the peripheral surfaces of all of the planet wheels and the axes of all of the planet wheels intersect at a common point along the longitudinal axis of the drive shaft since only in this case is a uniform pressure applied by the planet wheels to the cone of the shaft and vice versa. In addition, the conical surfaces of the ring against which the planet wheels roll must also be so formed that their generatrices coincide with the generatrices of the conical surfaces of the planet wheels at the region of which the planet wheels engage the stationary conical surfaces. The distance between the conical surface of the shaft and the conical surface of the planet wheel must also correspond exactly to the diameter of the planet wheels.

Because of the somewhat resilient character of the planet wheel carrier it is possible that the axis of one or another of the planet wheels will tilt out of its original or intended position so that the coincidence of the generatrices between the conical surfaces will no longer be maintained.

This will give rise to a so-called point contact between the planet wheels and the surfaces against which the planet wheels roll with correspondingly high wear in the limited contact region and binding and distortion within the transmission.

Furthermore, the very nature of the construction prevents miniaturization beyond a certain point because fabrication tolerances in general cannot be lowered without increasing play and binding forces within the transmission.

OBJECTS OF THE INVENTION

It is, therefore, the principal object of the present invention to provide an improved planetary transmission or drive of the friction type which is free from the drawbacks of the earlier devices of this type.

Another object of my invention is to provide a planetary friction drive which can be miniaturized and, in particular, can be used with great advantage in prosthetic devices.

It is also an object of the invention to provide a drive for the aforedescribed processes in which the pressing force of the planet wheels on the drive shaft can be established with precision and whereby fabrication tolerances can be readily compensated.

It is also an object of my invention to provide a comparatively low cost, highly miniaturizable planetary friction drive which is reliable and will not be subjected excessively to binding phenomenon.

SUMMARY OF THE INVENTION

These objects and others which will become apparent hereinafter are attained, in accordance with the invention by providing the planet wheels with cylindrical peripheries, i.e. peripheries with parallel generatrices.

According to the invention, the entrained plate or plate carrier is formed with entrained pins which are loosely received in the central bore of the planet wheels and the planet wheels are held in place on the conical region of the drive shaft by means of the ring, over the total length of the generatrices of the cylindrical peripheries of the planet wheels.

Specifically, therefore, the planetary friction wheels drive especially a miniature drive for a prostheses, can comprise:

a drive shaft;

means on the drive shaft forming a frustoconical surface coaxial with the drive shaft and rotatable therewith;

means defining an annular stationary surface spacedly surrounding the frustoconical surface;

a plurality of planet wheels received between the surfaces and frictionally rolling thereon, the planet wheels having central bores and respective cylindrical peripheries respectively coaxial with the bores;

a planet-carrier plate having entraining pins loosely traversing the bores and rotatably entrained by the planet wheels upon rotation of the shaft and rolling of the peripheries on the surfaces, the planet-carrier plate forming an output of the drive; and means for relatively adjusting the surfaces along an axis of the shaft and securing the surfaces in an axially adjusted position, the planet wheels being in contact with the frustoconical surface over entire lengths of respective generatrices of the cylindrical peripheries of the planet wheels.

As a result, the pressing force with which the planet wheels are held against the rolling surface can be attained directly by means of the ring and, because of the adjustability of the ring in the axial direction relative to the working shaft, the pressing force can be uniformly distributed to all of the planet wheels.

In the construction of the invention, the planet wheels are not rotatable about fixed axes with respect to the carrier or entrainment plate and do not rotate about any special axis whatsoever. Rather, the axis at any point in time is determined by the fact that the cylindrical peripheries uniformly engage the outer surface of the conical region of the working shaft so that the position of the axis of each planet wheel is variable in space, but the generatrices of the periphery of the planet wheels always are coincident with the generatrices of the conical region of the shaft or are parallel thereto.

Furthermore, the generatrices of all rolling surfaces of the planet wheels are parallel to one another.

The entrainment pins engage only loosely in the central bores of the planet wheels and do not in any way affect the orientation of the planet wheels. In this manner, it is possible to provide a planet wheel friction transmission with an overall diameter of 10 mm, i.e. to greatly miniaturize a friction drive so that it can be built into a prosthesis where, as is well known, space is highly limited.

I have suggested that it is known to provide planet wheels heretofore with cylindrical peripheries. However, in these constructions, the rolling surfaces of the shaft and the ring are likewise cylindrical so that the selection or adjustment of the pressing force upon the planet wheels is difficult since, once a certain force has been established, it no longer can be changed.

With an excessive small pressing force, the drive may slip whereas, with an excessive pressing force, deformation or damage of the material of the drive can occur. A further disadvantage of this construction is that because of fabrication tolerances, a shift of the drive shaft can occur which results in the formation of circumferential grooves therein resulting from and giving rise to a canting of the planet wheels. As a consequence, the drive shaft can be subject to tension or compression stresses and there is increased danger of binding. All of these drawbacks are avoided with the construction of the present invention.

Advantageously, the drive can have a sleeve which is coaxial with the drive shaft and stationary relative thereto and the ring can be mounted on the sleeve. The sleeve can be adjusted by a screw connection in the axial direction relative to a support and fixed in the desired position. In this manner a direct adjustment of the axial position of the ring with respect to the conical region of the drive shaft can be provided without requiring adjustment of the position of the drive shaft itself. In conventional constructions, adjustability of the distance between the drive shaft and the ring requires axial shifting of the entire bearing system for the drive shift in the housing.

According to a feature of the invention, the rolling surface of the ring opposite the drive shaft and against which the planet wheels bear as they roll, can be inwardly convex in an axial section, i.e. can bulge inwardly. This configuration of the rolling surface has been found to seat the planet wheels even more effectively against the conical region of the drive shaft.

To avoid undesired shifting of the planet wheels from the running surface of the ring, this running surface can be flanked by inwardly directed annular flanges.

In another advantageous feature of the invention, the conical region of the drive shaft can be axially shiftable relative to the motor shaft but angularly engaged or keyed therewith. A spline connection can thus be provided between the conical region and the motor shaft.

The conical region can be braced, in turn, against a support by a thrust bearing or the like which thus takes up the force applied to the conical region through the planet wheels by the ring. The motor shaft is thus maintained free from axial forces while axial forces can be maintained at desired levels between the planet wheels and the conical shaft region.

In a particular preferred embodiment to maintain uniform pressing forces, the thrust bearing can have a preferably continuous radially outwardly extending flange against which a compression spring bears. The opposite end of the compression spring is placed upon the support member. By a corresponding adjustment of the spring and of the sleeve, therefore, the spring can be prestressed or relieved to the desired degree. The pressing force is thus a function of the spring force so that thermal factors do not influence the pressing force in any material way.

BRIEF DESCRIPTION OF THE DRAWING

The above and other objects, features and advantages of my invention will become more readily apparent from the following description, reference being made to the accompanying highly diagrammatic drawing in which.

SPECIFIC DESCRIPTION

Figure 1:
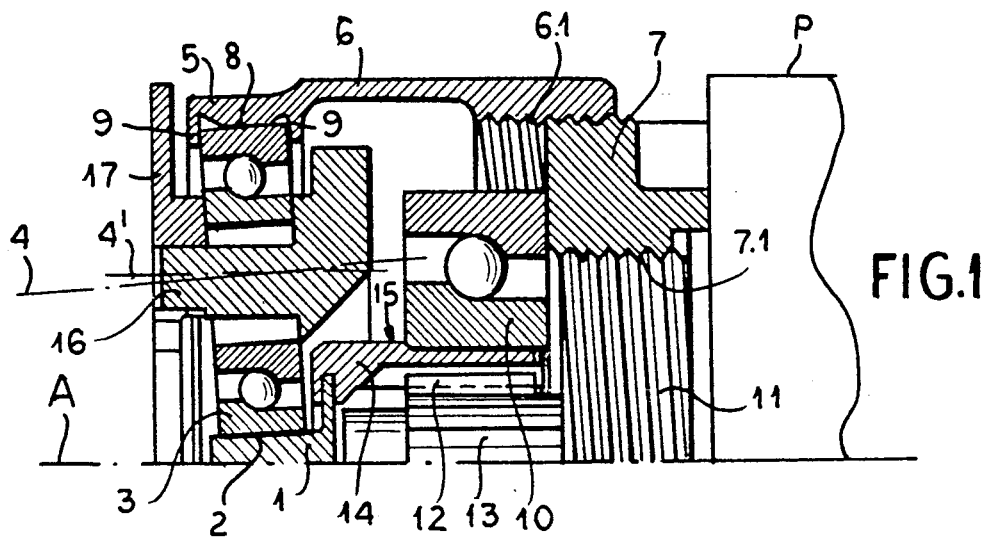
FIG. 1 is a partial axial section through a planet friction drive according to the invention in an embodiment in which the thrust bearing acts directly against the support element for the sleeve of the ring.

In the drawing, the member 1 of the drive shaft rotatable about an axis A is shown to be formed with a frustoconical running surface 2 for the planet wheels 3. The planet wheels 3 are held against the conical surface 2 by a ring 5 which is stationary. The ring 5, in turn, has a running surface 8 which engages the planet wheels 3 and which is inwardly and arcuately bulging as can be seen from FIGS. 1 and 2. The surface 8 can, if desired, also be frustoconical.

The ring 5 is formed on a sleeve 6 which is threadedly connected at 6.1 to a support member 7 which, in turn, can be fixed by a screw thread 7.1, for example, on a drive motor 11 which can be a miniature electric motor for driving an element of a prosthesis P to be attached to the entrainment plate 17 which represents the output shaft of the drive.

The motor 11 has a splined motor shaft 13 which thus has a tooth coupling 12 connecting it to a sleeve 14 carrying the portion 1 of the drive shaft formed with the conical surface 11. The spline coupling 12 allows axial displacement of the region 1 relative to the motor shaft 13 while ensuring a rotatable or angular coupling between the two parts.

The sleeve 14 has a shoulder 15 which, in the embodiment of FIG. 1, engages one race of a thrust bearing 10 whose other race is placed against the support 7.

The planet wheels 3 are pressed by the bulging surface 8 of the ring 5 against the conical surface 2 with a force determined by the tightening of the sleeve 6 onto the member 7. Slippage of the planet wheels 3 relative to the rings 5 is prevented by a pair of annular flanges 9 flanking the running surface 8 and engaging the planet wheels 3 between them.

Figure 2:
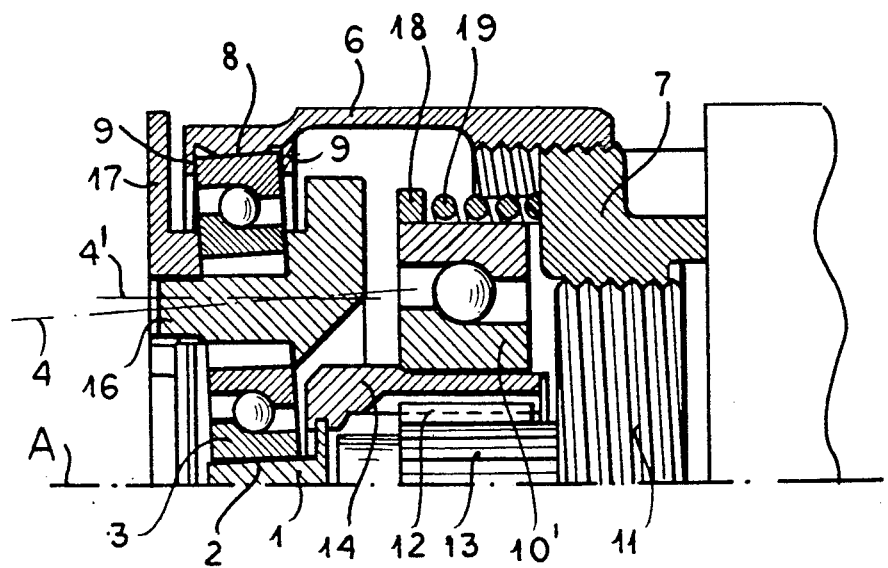
FIG. 2 is a view similar to FIG. 1 of an embodiment in which a compression spring is interposed between the thrust bearing in the support.
Figure 3:
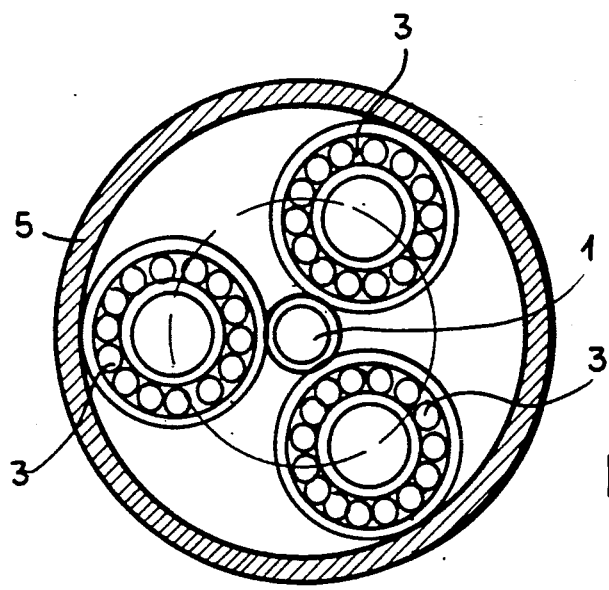
FIG. 3 is a diagrammatic cross section of the layout of the planet wheels with respect to the conical portion of the shaft and the ring.

The planet wheels 3 are formed, as can be seen in FIGS. 1 and 2 as ball bearings, in the central bores of which entrainment pins 16 can engage with substantial play. The pins 16 form a planet carrier with the entrainment plate 17.

The pins 16 are fixed to the plate 17.

As has been shown diagrammatically in FIGS. 1 and 2, the axes 4 of the entrainment pin 16 do not coincide with the axis 4 of the planet wheel 3 and the orientation of the latter axis can vary. The play between the pins 16 and the planet wheel 3 is such that the pins 16 cannot apply any canting forces to the planet wheels 3.

To adjust the pressing force of the planet wheel 3 against the conical outer surface 2 of the region 1 of the drive shaft, the sleeve 6 is screwed onto the support 7 until the desired force is achieved and entrainment of the output member 17 upon drive of the shaft 13 is obtained with the desired lack of slip on the rolling surfaces.

The counterforce is taken up directly by the thrust bearing 10 and the support 7.

In the embodiment of FIG. 2, which differs from that of FIG. 1, the thrust bearing 10' is provided with a continuous outwardly projecting annular flange 18. A compression spring 19 is seated against the radial flange 18 at one end and has its other end placed against the front face of the support 7. Between the support 7 and the thrust bearing 10, therefore, an intervening space is left so that the pressing force applied to the region 1 by the planet wheels 3 will be directly related to the force generated by the spring 19. The pressing force can thus be maintained constant by the stored force of the spring 19.

Of course, as the shaft 13 rotates, the rolling surface 2 frictionally entrains the wheels 3 so that the latter are rotated in senses opposite that of the shaft 13. The pins 16 are thus entrained in the same direction as the shaft 13 at a substantially slower speed but with increased torque in accordance with principles of planetary gear transmissions.

The conical friction drive of the invention is especially useful in prostheses or artificial joints where small space only is available for the speed reduction drive and for systems in which the force or movement must be taken off in the axial direction.

The axes 4 of the planet wheels here lie parallel to the generatrices of the conical surface 2 at the lines of contact between the planet wheels and the surface 2. In general, the axes of the planet wheels 3 are inclined to the axis of the drive shaft. Because of this parallelism of the generatrices, optimum force distribution is obtained. If the axes were to be parallel, of course, the planet wheels would engage the conical surface 2 with high edge pressure and could damage the surface 2.

I claim:
1. A planetary friction-wheel drive, comprising:
   a drive shaft rotatable about a first axis, said shaft being provided with a portion having a frustoconical surface coaxial with the drive shaft and rotatable therewith;
   an annular support formed with a stationary surface spacedly surrounding said frustoconical surface and being coaxial with said shaft;
   a plurality of planet wheels received between said surfaces and frictionally rolling thereon, said planet wheels having central bores extending along respective bore axes inclined to said first axis and respective cylindrical peripheries respectively coaxial with said bores;
   a planet-carrier plate having entraining pins loosely traversing said bores, said pins extending along respective second axes parallel to one another and to said first axis and being rotatably entrained by said planet wheels upon rotation of said shaft and rolling of said peripheries on said surfaces, said planet-carrier plate forming an output of the drive; and
   means for relatively adjusting said surfaces along said first axis of said shaft and for securing said surfaces in an axially adjusted position, said planet wheels being in contact with said frustoconical surface over entire lengths of respective generatrices of the cylindrical peripheries of said planet wheels.

2. The planetary friction-wheel drive defined in claim 1 wherein said support comprises a fixed sleeve formed with said annular stationary surface and coaxial with said shaft, a support for said sleeve, and screwthread means for interconnecting said sleeve and said support for said sleeve and forming said means for relatively adjusting said surfaces along said axis of said shaft and securing said surfaces in said axially adjusted position.

3. The planetary friction-wheel drive defined in claim 1 wherein said annular stationary surface is convexly curved in an axial section therethrough and bulges inwardly.

4. The planetary friction-wheel drive defined in claim 3, further comprising at least one inwardly projecting flange adjacent said annular stationary surface engageable with said planet wheels for limiting displacement thereof.

5. The planetary friction-wheel drive defined in claim 4 wherein two inwardly projecting annular flanges flank said annular stationary surface and confine said planet wheels between them.

6. A planetary friction-wheel drive comprising:
   a drive shaft rotatable about a rotation axis;
   a member on said shaft provided with a frustoconical surface and axially shiftable relative to said shaft and angularly entrained with said shaft;
   support means formed with an annular stationary surface spacedly surrounding said frustoconical surface of said member and coaxial with said shaft;
   a plurality of planet wheels received between said frustoconical and stationary surfaces and frictionally rolling thereon, said planet wheels being formed with respective central bores and with respective cylindrical peripheries respectively coaxial with said bores;
   a planet-carrier plate provided with entraining pins loosely traversing said bores and rotatably entrained by said planet wheels upon rotation of said shaft and rolling of said peripheries on said surfaces, said planet-carrier plate forming an output of the drive; and
   means for relatively adjusting said surfaces along said first axis of said shaft, said means for adjusting including an axial bearing bracing said member against a support in an axially adjusted position, said planet wheels being in contact with said frustoconical surface over entire lengths of respective generatrices of the cylindrical peripheries of said planet wheels.

7. The planetary friction-wheel drive defined in claim 6 wherein said axial bearing is formed with a flange projecting radially outwardly, said drive further comprising a compression spring braced between said support and said flange.

8. The planetary friction-wheel drive defined in claim 7 wherein said means for supporting comprises a fixed sleeve formed with said annular stationary surface and coaxial with said shaft, and screwthread means interconnecting said sleeve and said support and forming said means for relatively adjusting said surfaces along said axis of said shaft and securing said surfaces in said axially adjusted position.

9. The planetary friction-wheel drive defined in claim 8 wherein said annular stationary surface is convexly curved in an axial section therethrough and bulges inwardly.

10. The planetary friction-wheel drive defined in claim 9, further comprising at least one inwardly projecting flange adjacent said annular stationary surface engageable with said planet wheels for limiting displacement thereof.

11. The planetary friction-wheel drive defined in claim 10 wherein two inwardly projecting annular flanges flank said annular stationary surface and confine said planet wheels between them.

12. The planetary friction-wheel drive defined in claim 6, further comprising a motor driving said shaft and coaxial therewith, said support being provided on said motor.

* * * * *